United States Patent [19]

Niznick

[11] Patent Number: 5,062,800
[45] Date of Patent: Nov. 5, 1991

[54] DENTAL IMPLANT HANDLE, AND DENTAL IMPLANT PACKAGE INCLUDING A DENTAL IMPLANT HANDLE

[75] Inventor: Gerald A. Niznick, Encino, Calif.

[73] Assignee: Core-Vent Corporation, Encino, Calif.

[21] Appl. No.: 496,610

[22] Filed: Mar. 21, 1990

[51] Int. Cl.⁵ ............................................. A61C 5/00
[52] U.S. Cl. ..................................... 433/229; 433/173; 206/368
[58] Field of Search ............... 433/141, 173, 174, 175, 433/229; 206/368, 369

[56] References Cited

U.S. PATENT DOCUMENTS

| 4,027,392 | 6/1977  | Sawyer et al.    | 433/174   |
| 4,177,562 | 12/1979 | Miller et al.    | 433/174   |
| 4,234,309 | 11/1980 | Sellers          | 433/174 X |
| 4,915,629 | 4/1990  | Sellers          | 433/173   |
| 4,927,363 | 5/1990  | Schneider        | 433/173   |
| 4,955,811 | 9/1990  | Lazzara et al.   | 433/213 X |
| 4,976,617 | 12/1990 | Carchidi         | 433/141   |

FOREIGN PATENT DOCUMENTS

88/08283 11/1988 World Int. Prop. O. .......... 433/173

Primary Examiner—Robert P. Swiatek
Assistant Examiner—Nicholas D. Lucchesi

[57] ABSTRACT

A handle adapted for engaging, holding and delivering a dental implant to a surgical site, and for holding a dental implant within a package for the implant comprises a body section with a middle portion adapted to fit into a container for the implant; a flange portion connected to the middle portion and adapted to engage an opening in the implant container; a first end portion connected to the middle portion and including an implant-engaging configuration internal or external to the handle; and a second end portion connected to the flange and including a configuration suitable for engaging an implant-insertion tool. The body portion includes an internal passage adapted to receive a shaft that includes a portion for securing an implant to the handle at the implant-engaging configuration.

15 Claims, 2 Drawing Sheets

DENTAL IMPLANT HANDLE, AND DENTAL IMPLANT PACKAGE INCLUDING A DENTAL IMPLANT HANDLE

BACKGROUND OF THE INVENTION

This invention relates to a handle for dental implants, and a package for dental implants that includes such a handle.

A need exists for a dental implant package that allows delivery of a dental implant to a surgical site in a patient's jaw without touching or otherwise contacting the implant. This invention provides a handle for a dental implant that can be attached to such an implant before cleaning or sterilizing of the implant. The handle thus minimizes the need to touch or contact the implant after cleaning and sterilizing.

SUMMARY OF THE INVENTION

In preferred embodiments, the handle functions as a stopper for a dental implant container and as a means for engaging an insertion tool and delivering the implant to a patient's jawbone without touching or otherwise contacting the implant.

Thus, the invention provides a handle for engaging and holding a dental implant, and for delivering such an implant to a surgical site, as in the jawbone of a patient. The handle comprises a body section including a middle portion adapted to fit into a container or vial for the implant. Connected to the middle portion is a flange portion adapted to engage and close an opening in the container. When placed in a container opening, the flange portion sealingly encloses an implant attached to the handle within the container.

A first end portion connected to the middle portion of the handle includes implant-engaging means. In preferred embodiments, the implant-engaging means comprises an irregularly-configured portion that engages a complementary, irregularly-shaped portion on the implant itself. This irregularly-shaped portion in the first end portion can be a multi-sided configuration formed inside an opening in the first end portion, or a multi-sided configuration formed on the outside of this second end portion.

The body section of the handle includes a second end portion connected to the flange portion that includes means for engaging devices that insert an implant in a surgical site such as ratchets, screwdrivers, Allen wrenches and the like.

The body portion includes an internal passage adapted for receiving shaft means. The shaft means is adapted to secure a dental implant to the implant-engaging means. To this end, the shaft means is preferably a threaded shaft that screws into an internally-threaded passage in a dental implant. Alternatively, this shaft can have a friction-fit member at the dental implant-engaging end where the dental implant itself has a complementary friction-fit configuration. In preferred embodiments, the internal passage also includes a threaded portion to engage complementary threads on the shaft means to further secure the implant to the implant-engaging means at the first end portion of the handle.

In preferred embodiments, the means for engaging implant-insertion devices includes a projection, preferably a multi-sided projection, connected to the flange portion. In some of these embodiments, this projection is connected to the flange portion through a neck means having a smaller circumference than the projection, and preferably adapted to engage a clamp or other tool for holding the handle firmly. In other embodiments, this projection includes a groove for receiving an O-ring or other washer to permit engagement with an implant insertion tool.

The handle is adapted to engage and hold dental implants that have external irregularities such as the Swede-Vent TM dental implant and the Branemark dental implant and dental implants that have internal irregularities in an internal passage at one end of the implant such as the Core-Vent® dental implant, the Screw-Vent® dental implant, and the Micro-Vent® dental implant.

The package of this invention includes the handle for the dental implant and a container of a size and shape adapted to engage and hold the handle in place as a stopper for the container. Preferably, this container is made of radiation-transmissive glass or plastic and is adapted for enclosure within another container so that the first container can be maintained in sterile condition after irradiation.

BRIEF DESCRIPTION OF THE DRAWINGS

This invention can better be understood by reference to the drawings, in which.

DETAILED DESCRIPTION OF THE DRAWINGS

Figure 1:
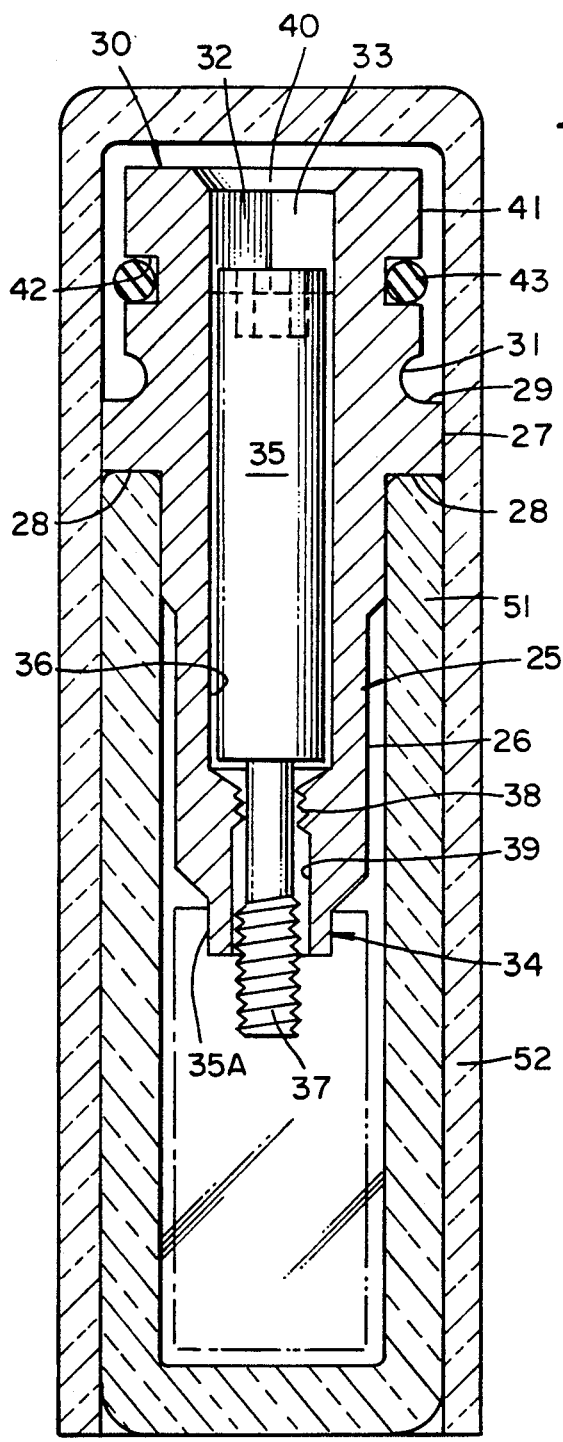
FIG. 1 shows a side elevation view, in cross-section, of a first embodiment of a handle adapted for use with a dental implant having an internal irregularity in a passage within the implant, such as the Core Vent® dental implant.
Figure 2:
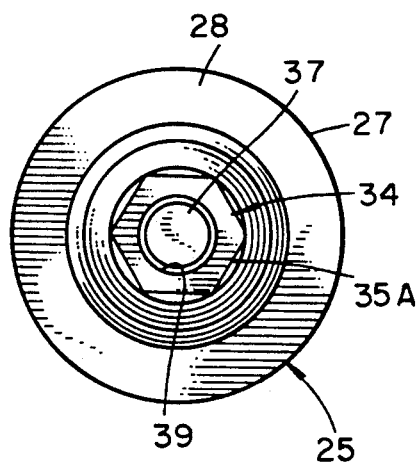
FIG. 2 is an elevation view of one end of the handle embodiment shown in FIG. 1.
Figure 3:
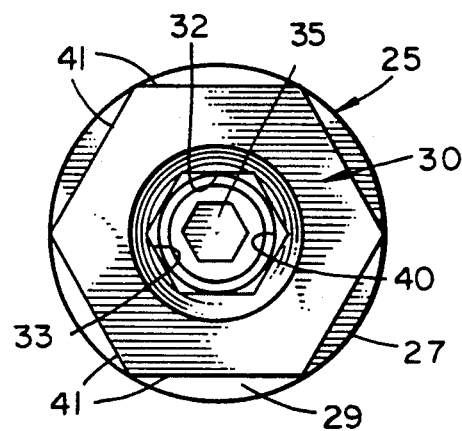
FIG. 3 is an end elevation view of the other end of the handle embodiment shown in FIGS. 1 and 2.

FIGS. 1-3 show a first embodiment, generally designated 25, of the new handle. Handle 25 includes middle portion 26, which is generally cylindrical in shape, and is of a size and shape adapted to fit within a complementary-shaped opening in a vial or container 51 for the handle, and for an implant attached to the handle. Flange 27 includes, along its lower surface 28, a surface for engaging handle 25 within an opening at the rim of container 51 for the handle and for an attached dental implant. Container 51, and handle 25, are sterilized and fully enclosed within a second container 52.

Attached to the upper surface 29 of flange 27 is projection 30, joined to flange surface 29 through neck portion 31. Neck portion 31 is of smaller circumference than projection 30, and is of a size and shape adapted for engaging a tool such as clamp to hold the handle in place. Projection 30 has an outer, multi-sided configuration 41 suitable for engaging an implant-insertion tool such as a wrench. Projection 30 also includes groove 42 for receiving O-ring 43. With O-ring 43 in place, projection 30 is adapted to engage frictionally an implant insertion device at O-ring 43.

Inside opening 40 of projection 30 is a multi-sided configuration including sides 32 and 33 for engaging a tool such as an Allen wrench for carrying the handle and implant to a surgical site, and for threading the implant into the site. At the other end of middle portion 26 is end portion 34. End portion 34 includes an external, irregularly-shaped configuration 35A, which fits within and engages a complementary, irregularly-shaped portion inside a passage in a dental implant such as a Core-Vent® dental implant. The implant is secured against end portion 34 by shaft 35, which fits within internal passage 36 in handle 25. Shaft 35 includes threaded portion 37 which engages internal threads 38, in internal passage 36, and threads internal to an implant seated on end portion 34, where shaft 35 extends into opening 39. Shaft 35 thus holds the implant against the implant-engaging section 34 of handle 25.

Figure 4:
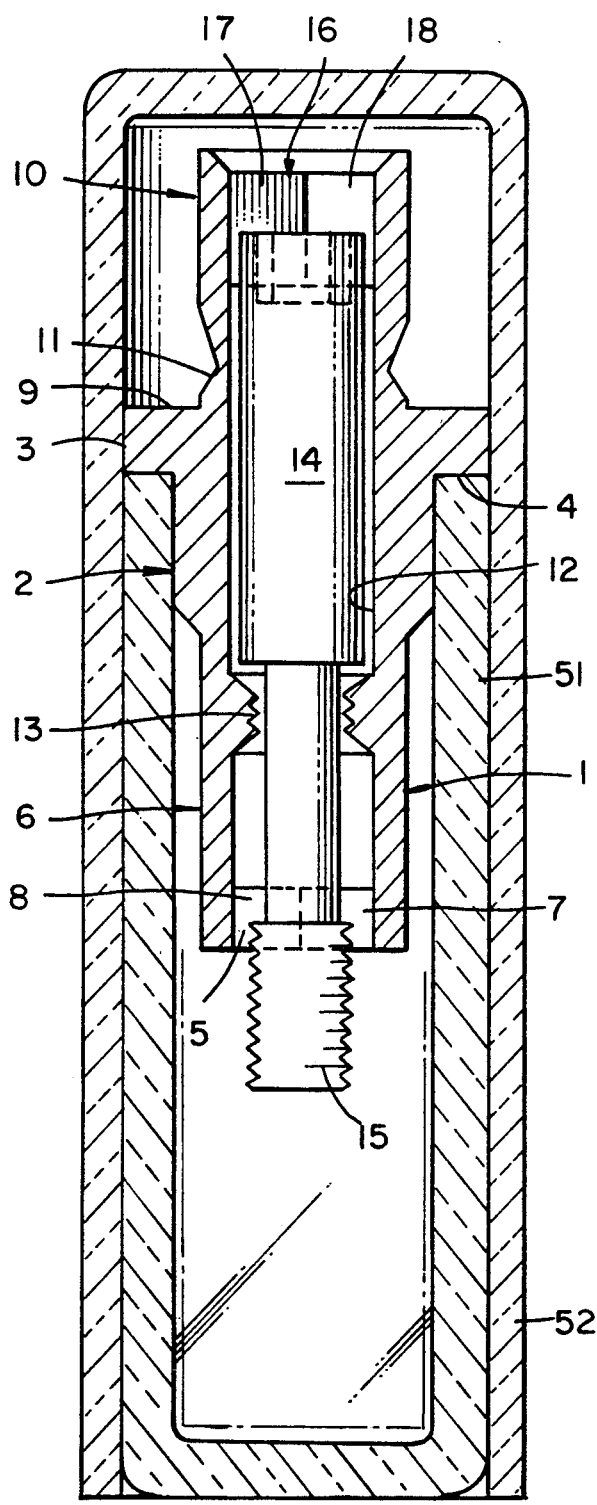
FIG. 4 shows a side elevation view, in cross-section, of a second embodiment of a handle adapted for use with a dental implant having an external irregularity for gripping and inserting the implant in a surgical jawbone site, such as the Swede-Vent TM dental implant.
Figure 5:
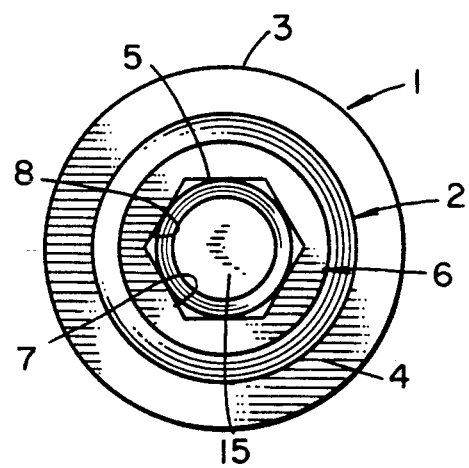
FIG. 5 is an elevation view of one end of the handle embodiment shown in FIG. 4.
Figure 6:
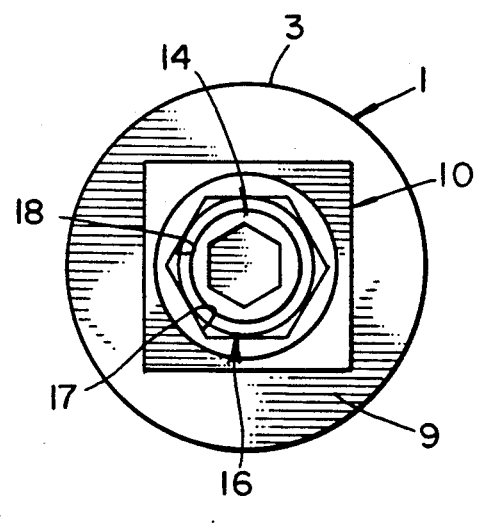
FIG. 6 is an elevation view of the other end of the handle embodiment shown in FIG. 5.

FIGS. 4–6 show a second embodiment generally designated 1 of a handle adapted to engage and hold dental implants. This handle includes a middle portion 2 of a size, shape and configuration, here generally cylindrical, to fit snugly within the opening in a container or vial 51 for an implant on the handle.

Connected to middle portion 2 is flange portion 3, whose lower surface 4 seats against the rim of an opening in an implant container 51 to enclose such an implant within the container. Middle portion 2 is also connected to end portion 6 that includes opening 5. Within opening 5 is a multi-sided, implant-engaging irregular configuration including sides 7 and 8 shown in FIG. 1. This multi-sided configuration engages an external flange on a dental implant such as the Swede-Vent ™.

Handle 1 also includes, connected to upper surface 9 of flange 3, a multi-sided projection member 10. Linking flange 3 and multi-sided projection 10 is neck section 11, which is of a size and shape adapted to receive and engage a tool such as a clamp.

Projection 10 includes an opening 16 which has a multi-sided internal configuration including sides 17 and 18. This multi-sided configuration within opening 16 is adapted to engage an implant-insertion tool such as an Allen wrench or other tool.

Inside handle 1 is internal, longitudinally extending passage 12. Passage 12 includes threaded region 13 which engages a threaded portion 15 of shaft 14. Shaft 14 is of a size and shape adapted to fit within passage 12, and includes threaded portion 15 which engages internal threads 13 and threads in an internal passage within a dental implant. The dental implant is held in opening 5 by the multi-sided internal configuration that includes sides 7 and 8, and by threads 15 on shaft 14, which engage the internal threads in a passage at the top of the implant.

What is claimed is:

1. A handle adapted for holding a dental implant comprises a body section including a middle portion adapted to fit within and to close a container for said implant, a first end portion connected to said middle portion and including implant-engaging means comprising a multi-sided configuration adapted to engage a complementary multi-sided configuration on a dental implant, and a second end portion connected to said middle portion and including means for engaging an implant insertion device, said body section having an internal passage adapted for receiving shaft means adapted for connecting said implant to said implant-engaging means, and shaft means including means for holding an implant to said implant-engaging means when said shaft means is inserted into said internal passage, and connected to an implant.

2. The handle of claim 1 wherein said second end portion includes projection means connected to said middle portion by neck means, said neck means having a smaller circumference than said projection means.

3. The handle of claim 2 wherein said passage has an opening in said projection means, and within said opening in said projection means is an irregularly-shaped inplant insertion means.

4. The handle of claim 1 wherein said internal passage comprises threads, and said shaft means includes complementary threads to engage said passage threads.

5. The handle of claim 1 wherein said second end portion includes groove means, and, within said groove means, an O-ring adapted to engage said implant insertion device.

6. The handle of claim 1 wherein said multi-sided configuration lies in an opening at said first end portion.

7. The handle of claim 1 wherein said multi-sided configuration lies on the exterior surface of a projection on said first end portion.

8. A package for a dental implant includes a container for a dental implant, and a stopper for said container, said stopper comprising a handle for a dental implant, said handle comprising a body portion section including a middle portion adapted to fit into a container for said implant, a flange portion connected to said middle portion and adapted to engage an opening in said container, a first end portion connected to said middle portion and including implant-engaging means, a second end portion connected to said flange portion and including means for engaging an implant insertion device, said body portion having an internal passage adapted for receiving shaft means adapted for connecting said implant to said implant-engaging means.

9. The package of claim 8 wherein said container is radiation transmissive.

10. The package of claim 8 wherein said container is sterilized, and is enclosed within a second container.

11. The package of claim 8 wherein said second end portion includes groove means, and within, said groove means, an O-ring adapted to engage said implant insertion device.

12. The package of claim 8 wherein said implant-engaging means comprises a multi-sided configuration adapted to engage a complementary multi-sided configuration on a dental implant.

13. The package of claim 12 wherein said multi-sided configuration lies within an opening at said first end portion.

14. The package of claim 12 wherein said multi-sided configuration lies on the exterior surface of a projection on said first end portion.

15. The package of claim 8 further comprising shaft means adapted for insertion into said internal passage, said shaft means including means for connecting said implant to said implant-engaging means.

* * * * *